(12) United States Patent
Lensing et al.

(10) Patent No.: US 6,933,158 B1
(45) Date of Patent: Aug. 23, 2005

(54) METHOD OF MONITORING ANNEAL PROCESSES USING SCATTEROMETRY, AND SYSTEM FOR PERFORMING SAME

(75) Inventors: Kevin R. Lensing, Austin, TX (US); James Broc Stirton, Austin, TX (US); Homi E. Nariman, Austin, TX (US); Steven P. Reeves, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 166 days.

(21) Appl. No.: 10/285,041

(22) Filed: Oct. 31, 2002

(51) Int. Cl.[7] ............................................. H01L 21/66
(52) U.S. Cl. ........................ 438/16; 438/17; 438/308; 438/514
(58) Field of Search ................................ 356/445–448; 438/4, 14, 16, 17, 308, 514, 524

(56) References Cited

U.S. PATENT DOCUMENTS

| 4,188,123 | A | * | 2/1980 | Kleinknecht ................ 356/521 |
| 5,011,794 | A | * | 4/1991 | Grim et al. .................. 438/796 |
| 5,105,362 | A | * | 4/1992 | Kotani ........................ 700/108 |
| 5,604,581 | A | * | 2/1997 | Liu et al. ..................... 356/73 |
| 5,867,276 | A |   | 2/1999 | McNeil et al. .............. 356/445 |
| 5,877,860 | A |   | 3/1999 | Borden ....................... 356/376 |
| 5,880,838 | A |   | 3/1999 | Marx et al. ................. 356/351 |
| 5,900,633 | A | * | 5/1999 | Solomon et al. ........ 250/339.08 |
| 6,051,348 | A |   | 4/2000 | Marinaro et al. ............ 430/30 |
| 6,081,334 | A |   | 6/2000 | Grimbergen et al. ....... 356/357 |
| 6,245,584 | B1 |  | 6/2001 | Marinaro et al. ............ 438/14 |
| 6,433,878 | B1 |  | 8/2002 | Niu et al. .................... 356/603 |
| 6,660,543 | B1 | * | 12/2003 | Stirton et al. ............... 438/16 |
| 2002/0135781 | A1 | | 9/2002 | Singh et al. ................. 356/601 |

OTHER PUBLICATIONS

U.S. Appl. No. 09/824,156, filed Apr. 2, 2001, Stirton.

* cited by examiner

*Primary Examiner*—Asok Kumar Sarkar
(74) *Attorney, Agent, or Firm*—Williams, Morgan & Amerson

(57) ABSTRACT

The present invention is directed to several inventive methods of monitoring anneal processes performed on implant regions, and a system for accomplishing same. In one aspect, the method comprises forming a first plurality of implant regions in a semiconducting substrate, performing at least one anneal process on implant regions, performing a scatterometric measurement of at least one of the implant regions after at least a portion of the anneal process is performed to determine a profile of the implant region and determining an effectiveness of the anneal process based upon the determined profile of the implant region. In other embodiments, one or more parameters of the anneal process may be varied on subsequently processed substrates based upon the determined efficiency of the anneal process.

84 Claims, 4 Drawing Sheets

(Post implant)

(Post anneal)

Figure 5A (Post implant)

Figure 5B (Post anneal)

METHOD OF MONITORING ANNEAL PROCESSES USING SCATTEROMETRY, AND SYSTEM FOR PERFORMING SAME

BACKGROUND OF THE INVENTION

1. Field of the Invention

This invention is generally directed to the field of semiconductor processing, and, more particularly, to a method of monitoring anneal processes performed on implant regions, and a system for performing same.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

During the course of manufacturing integrated circuit devices, a variety of doped regions may be formed in a semiconducting substrate. Typically, these doped regions are formed by performing an ion implant process wherein a dopant material, e.g., arsenic, phosphorous, boron, boron difluoride, etc., is implanted into localized areas of the substrate. For example, for CMOS technology, various doped regions, sometimes referred to as wells, are formed in the substrate. The wells may be formed using either N-type or P-type dopant atoms. After the wells are formed, semiconductor devices, e.g., transistors, may be formed in the region defined by the well. Of course, other types of doped regions may also be formed in modem semiconductor manufacturing operations.

As modem device dimensions continue to shrink, the implant profiles of the various doped regions become very important. That is, as device dimensions shrink, parameters of the doped region, such as depth, width, dopant concentration profile, etc., become more important. Small variations in one or more of these parameters may adversely affect device performance. For example, if well implants in a given device are formed too shallow or not formed deep enough, the devices formed in the wells may exhibit excessive leakage currents.

After implant regions are formed in a substrate, one or more anneal processes are performed to activate the implanted dopant atoms and to repair the damage to the lattice structure due to the ion implantation process. The temperature and duration of the anneal process may vary depending on the application. Moreover, the anneal process may be performed in either a furnace or a rapid thermal anneal (RTA) chamber. For example, where an RTA chamber is employed, the anneal process may be performed at a temperature ranging from approximately 1000–1200° C. for a duration anywhere from 10 seconds to 2 minutes.

During this anneal process, the implanted dopant atoms tend to migrate within the substrate in an approximately isotropic fashion.

The effectiveness of such anneal processing is normally monitored in an effort to insure that the implant regions are correctly formed such that they may function as intended. For example, for CMOS technology, various doped regions, sometimes referred to as wells, arc formed in the substrate. The wells may be formed using either N-type or P-type dopant atoms. After the wells are formed, semiconductor devices, e.g., transistors, may be formed in the region defined by the well. Of course, other types of doped regions may also be formed in modem semiconductor manufacturing operations.

As modern device dimensions continue to shrink, the implant profiles of the various doped regions become very important. That is, as device dimensions shrink, parameters of the doped region, such as depth, width, dopant concentration profile, etc., become more important. Small variations in one or more of these parameters may adversely affect device performance. For example, if well implants in a given device are formed too shallow or not formed deep enough, the devices formed in the wells may exhibit excessive leakage currents.

After implant regions are formed in a substrate, one or more anneal processes are performed to activate the implanted dopant atoms and to repair the damage to the lattice structure due to the ion implantation process. The temperature and duration of the anneal process may vary depending on the application. Moreover, the anneal process may be performed in either a furnace or a rapid thermal anneal (RTA) chamber. For example, where an RTA chamber is employed, the anneal process may be performed at a temperature ranging from approximately 1000–1200° C. for a duration of approximately 5–10 seconds. During this anneal process, the implanted dopant atoms tend to migrate within the substrate in an approximately isotropic fashion.

The effectiveness of such anneal processing is normally monitored in an effort to insure that the implant regions are correctly formed such that they may function as intended. To that end, one or more electrical tests may be performed to monitor the efficiency of the anneal process. In one example, one or more sheet resistance tests may be performed on one or more implant regions after the anneal process is performed, and from those results, the effectiveness of the anneal process is inferred. That is, for example, if, after the anneal process is performed, the implant region exhibits a sheet resistance value within certain limits, then the anneal process is deemed to be successful. Other electrical tests may be performed on the implant regions after the anneal process is performed to determine the effectiveness of the anneal process, e.g., capacitance-voltage measurement to determine the dopant profile. Parameters such as the depth of the implant regions may also be determined by employing various physical measurement techniques, e.g., so-called angle lap and stain techniques, groove and stain techniques, etc. In some cases, the implant regions may be cross-sectioned and inspected with the aid of microscopes. Moreover, in some cases, test wafers are manufactured for the purpose of performing such tests.

While the aforementioned techniques may be useful, they do have some drawbacks. For example, such testing can be very time-consuming, and the results of such testing may not be available as quickly as would otherwise be desired. Moreover, in some cases, the resulting profile of the implant region is assumed based upon the measurement results, e.g., resistance. That is, the testing methodology does not, in some cases, provide for direct measurement of the profile of the implant region; rather, such profile is inferred based upon the results of the test data.

The present invention is directed to various methods that may solve, or reduce, at least some of the problems described above.

SUMMARY OF THE INVENTION

In one aspect, the present invention is directed to various methods of monitoring anneal processes performed on implant regions. In one illustrative embodiment, the method comprises forming a first plurality of implant regions in a semiconducting substrate, performing at least one anneal process on said implant regions, performing a scatterometric measurement of at least one of the implant regions after at least a portion of the anneal process is performed to determine a profile of the implant region and determining an effectiveness of the anneal process based upon the determined profile of the implant region. In further embodiments, the method comprises modifying, based upon the determined effectiveness of the anneal process, at least one parameter of an anneal process to be performed on implant regions formed on a subsequently processed substrate.

In another illustrative embodiment, the method comprises forming a first plurality of implant regions in a semiconducting substrate, performing at least one anneal process on the first plurality of implant regions, and performing a scatterometric measurement of at least one of the first plurality of implant regions after the anneal process is completed to determine an implant profile of at least one implant region by generating a profile trace for at least one implant region, creating a plurality of profile traces, each of which correspond to an anticipated profile of at least one implant region, and comparing the generated profile trace to at least one created profile trace. The method further comprises determining an effectiveness of at least one anneal process based upon the determined profile of at least one implant region.

In yet another illustrative embodiment, the method comprises forming a first plurality of implant regions in a semiconducting substrate, performing at least one anneal process on the first plurality of implant regions, and performing a scatterometric measurement of at least one of the first plurality of implant regions after the anneal process is completed to determine an implant profile of at least one implant region by generating a profile trace for at least one implant region, creating a target profile trace for at least one implant region and comparing the generated profile trace to the target profile trace. The method further comprises determining an effectiveness of at least one anneal process based upon the determined profile of at least one implant region.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device and the doped regions are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods of monitoring anneal processes performed on implant regions, and a system for accomplishing same. In some embodiments, the anneal process or processes are performed in a furnace or a rapid thermal anneal (RTA) chamber. In even further embodiments, based upon the results of such monitoring, the effectiveness of the anneal process may be evaluated and/or one or more of the parameters of the anneal process may be modified on subsequently processed substrates As will be readily apparent to those skilled in the art upon a complete reading of the present application, the present invention may be employed in connection with a variety of different process tools that are capable of performing a heat treating or anneal process on an implant region, and the present invention may also be employed with respect to implant regions comprised of any type of dopant material, e.g., N-type or P-type dopant materials. Lastly, the present methods are applicable to a variety of technologies, e.g. NMOS, PMOS, CMOS, etc., and is readily applicable to a variety of devices, including, but not limited to, logic devices, memory devices, etc.

The present invention is related to a previously filed application, Ser. No. 09/824,156, entitled "Method of Measuring Implant Profiles Using Scatterometric Techniques," filed Apr. 2, 2001. That application is currently assigned to the assignee of the present invention, Advanced Micro Devices, Inc. The present invention is also related to application Ser. No. 10/284,996, now a U.S. Pat. No. 6,660,543, entitled "Method of Measuring Implant Profiles Using Scatterometric Techniques Wherein Dispersion Coefficients are Varied Based Upon Depth," filed concurrently with the present application.

Figure 1:
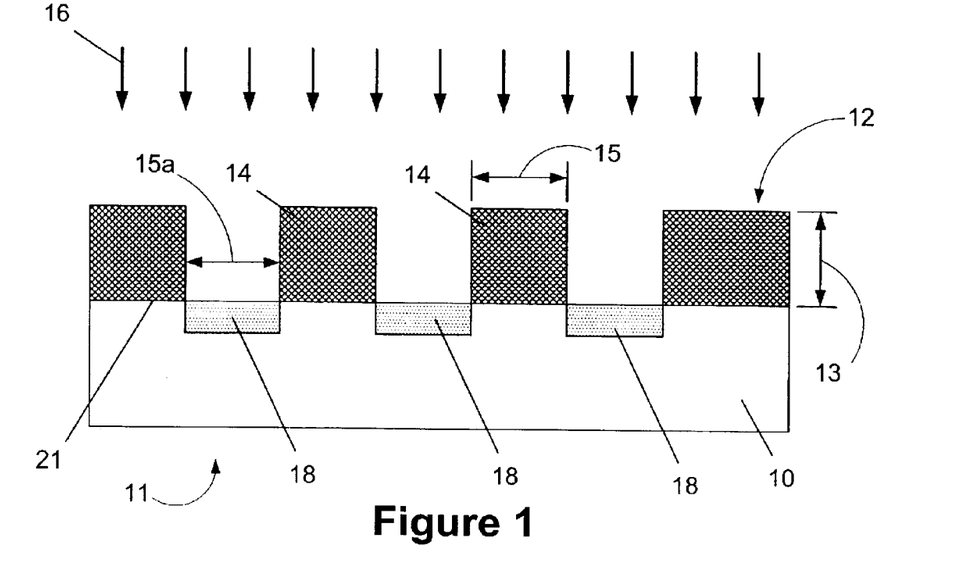
FIG. 1 is a cross-sectional view of a portion of a substrate having a plurality of implant regions formed therein, and a patterned layer of photoresist positioned above the substrate.

FIG. 1 depicts an illustrative structure 11 that may be used in accordance with the present invention. The structure 11 is formed on part of a wafer comprised of, for example, silicon. As will become clear upon a complete reading of the present application, the structure 11 may be a test structure, or it may be part of an actual production integrated circuit device. As shown in FIG. 1, a patterned layer of photoresist 12 is formed above a semiconducting substrate 10. The patterned layer of photoresist 12 has a plurality of photoresist features 14 defined therein. An ion implantation process, as indicated by arrows 16, is used to form a plurality of implant regions 18 in the areas of the substrate 10 not covered by the patterned layer of photoresist 12.

The patterned layer of photoresist 12 may be formed by a variety of known photo-lithography techniques. For example, the patterned layer of photoresist 12 may be comprised of a negative or a positive photoresist. The thickness 13 of the patterned layer of photoresist 12 may be varied as a matter of design choice. In one illustrative embodiment, the patterned layer of photoresist 12 has a thickness 13 that ranges from approximately 1.0–2.5 $\mu$m (10,000–25,000 Å). Moreover, the features 14 in the patterned layer of photoresist 12 may have a width 15 that may be varied as a matter of design choice. The spacing 15a between the photoresist features 14 may also vary. The ion implantation process may be performed by a variety of tools used in modern semiconductor fabrication facilities for performing such operations. Moreover, the implant energy, the dopant material implanted, the concentration of dopant material, as well as the implant angle, may he varied in forming the implant regions 18 in the substrate 10.

Figure 2:
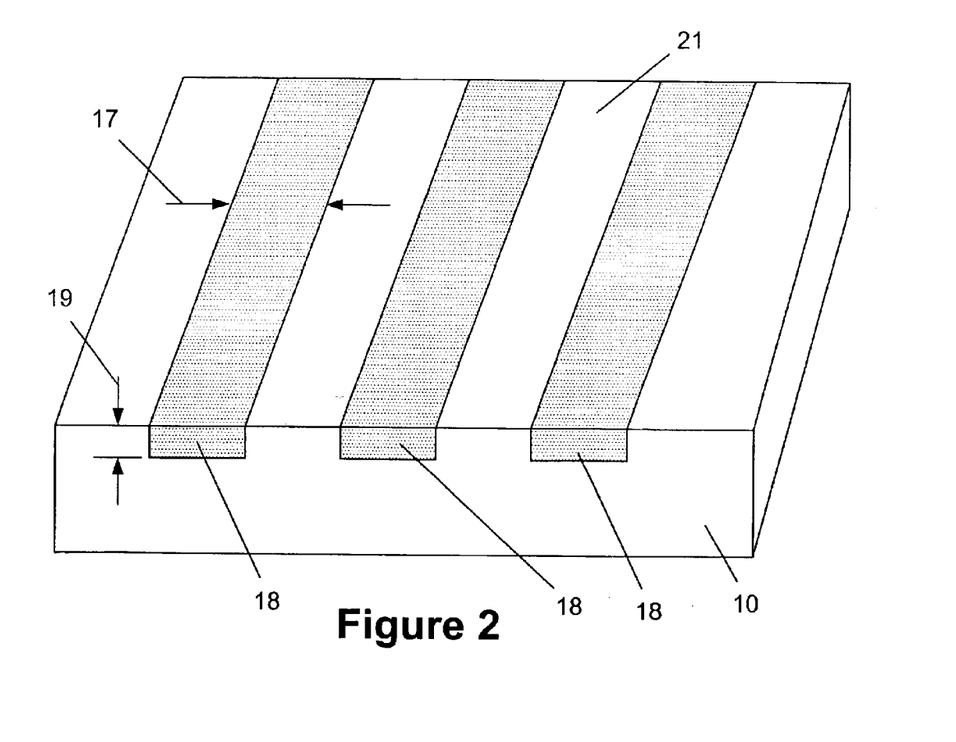
FIG. 2 is an isometric view of the structure depicted in FIG. 1 with the layer of photoresist removed.

FIG. 2 is an isometric view of the substrate 10, and the implant regions 18, shown in FIG. 1 after the patterned layer of photoresist 12 is removed, or stripped, using a variety of known techniques, e.g., ashing. More particularly, as shown in FIGS. 1 and 2, each of the implant regions 18 has a width 17 and a depth 19 beneath the surface 21 of the substrate 10. As will be recognized by those skilled in the art after a complete reading of the present application, the implant regions 18 constitute a grating pattern that may be measured using scatterometric techniques. In some cases, such a grating pattern may be formed in the scribe lines of a semiconducting substrate. The number of these implant regions 18 that may be formed on an actual device may vary. For example, the grating pattern may be formed in a 100 nm×120 nm region in which approximately 300–400 implant regions 18 are formed (the length of which are parallel to the short side of the region).

Figure 3:
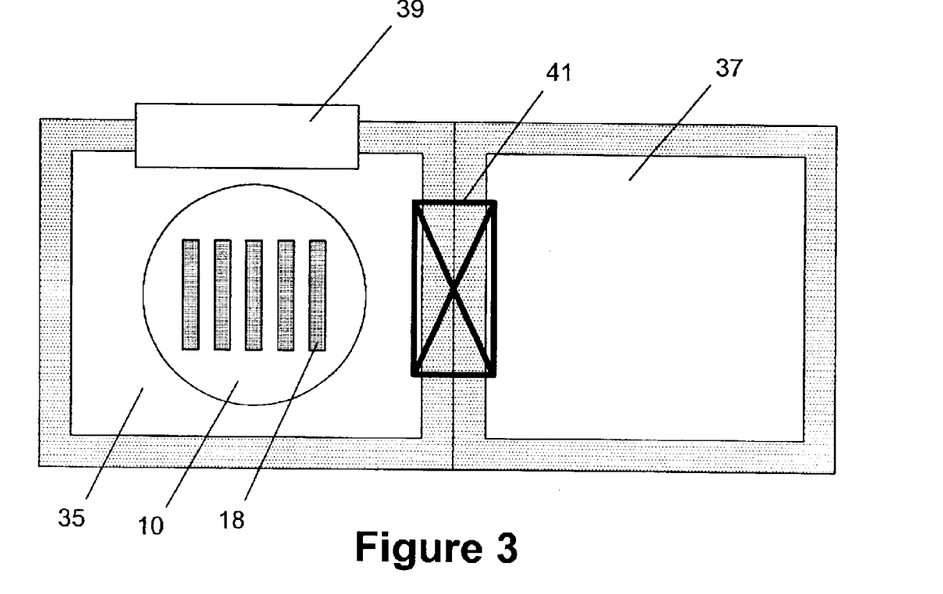
FIG. 3 is a schematic depiction of an illustrative anneal tool having a substrate positioned therein.

The implant regions 18 depicted in FIGS. 1 and 2 reflect the as-implanted location of those regions. However, as stated previously, the implant regions 18 will be subjected to one or more heat treatment or anneal processes to activate the implanted dopant material and to repair damage to the lattice structure of the substrate. As used herein, the term anneal should be understood to refer to any type of heating process at any level of temperature. FIG. 3 is a schematic depiction of an illustrative anneal tool 35 having a substrate 10 positioned therein. A plurality of implant regions 18 have been formed in the substrate 10 as depicted in the drawing. The anneal tool 35 may be any type of tool capable of performing a heat treatment process on the implant regions 18. For example, the anneal tool 35 may be a furnace or a rapid thermal anneal (RTA) chamber.

In general, a scatterometry-based tool will be used to measure various aspects of the implant regions 18 before, after and/or during the anneal process performed in the anneal tool 35. To that end, in some embodiments, a separate measurement module 37 may be operatively coupled to the anneal tool 35 such that, when desired, one or more substrates in the anneal tool 35 may be transported to the measurement module 37 (by a variety of known robotic handling devices (not shown)) where the implant regions 18 will be measured using a scatterometry tool. A schematically depicted gate 41 may be provided between the anneal tool 35 and the measurement module 37. The gate 41 may be opened as necessary to allow the substrate 10 to be removed from the anneal tool 35 to the measurement module 37. In other embodiments, the anneal tool 35 may be provided with a schematically depicted window 39 through which scatterometric measurements of the implant regions 18 may be made. Of course, the present invention may also be employed in cases where substrates 10 processed in the anneal tool 35 are physically removed from the anneal tool 35 and taken to a separate location where the scatterometric measurements may be made.

Figure 4:
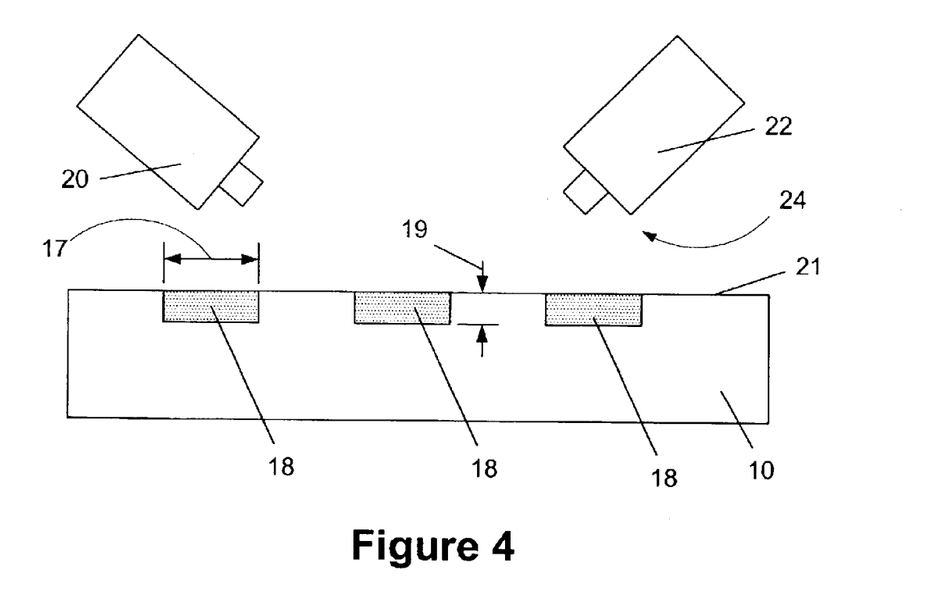
FIG. 4 is a cross-sectional view of the device shown in FIG. 1 after the patterned layer of photoresist has been removed.

As stated previously, scatterometric techniques will be used to measure the implant profiles of the implant regions 18. As used herein, measuring the implant profile of the implant region 18 means measuring one or more characteristics of the implant region 18, e.g., depth, width, dopant concentration, etc. For example, the implant profiles may reflect dopant concentration levels at various depths into a substrate. A variety of scatterometry type tools may be used with the present invention, e.g., so-called 2θ-type systems and lens-type scatterometry tools. An illustrative scatterometry tool 24 comprised of a light source 20 and a detector 22 is schematically depicted in FIG. 4. In general, the light source 20 is used to illuminate the structure 1, and the detector 22 takes optical measurements, such as intensity, of the reflected light. The scatterometry tool 24 may use white light, or some other wavelength or combination of wavelengths, depending on the specific implementation. Typically, the light source 20 will generate an incident beam that has a wide spectral composition and wherein the intensity of the reflected light changes slowly in comparison to changes in wavelength. The angle of incidence of the light may also vary, depending on the specific implementation. For example, a spectroscopic ellipsometer (single angle, many wavelengths), or a laser (single wavelength, many angles) may be used with the present invention. Additionally, the light source 20 and the detector 22 may be arranged in a concentric circle configuration, with the light source 20 illuminating the structure 11 from a perpendicular orientation, e.g., a reflectometer. The intensity of the reflected light may be measured as s-and p-polarization over either multiple angles or at multiple wavelengths.

In general, the scatterometry tool 24 (see FIG. 4) includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc.

Figure 5A:
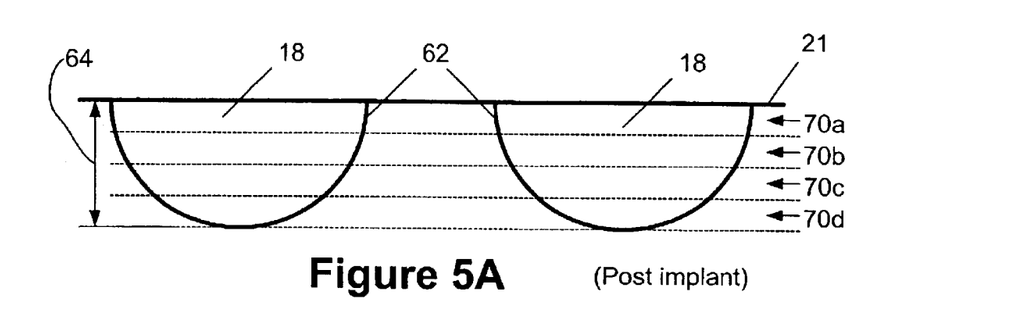
FIGS. 5A and 5B are illustrative depictions of implant regions post-implant and post-RTA, respectively.
Figure 5B:
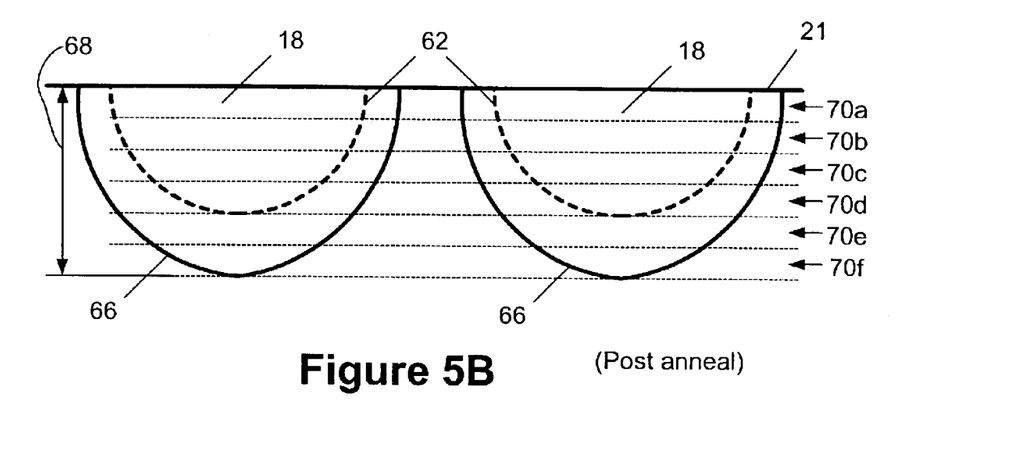

The implant regions 18 are schematically depicted in FIGS. 1–2 and 4 as having a generally rectangular cross-sectional configuration. FIGS. 5A–5B are enlarged views of the implant regions 18 wherein the implant regions 18 have a more realistic, non-rectangular implant profile. Even more specifically, FIGS. 5A–5B depict the implant profiles post-implant (FIG. 5A) and post-anneal (FIG. 5B). As is well known to those skilled in the art, after the implant regions 18 are initially formed in the substrate, one or more anneal processes may be performed to activate the implanted dopant material and/or to repair the damage to the lattice structure resulting from the ion implant process performed to form the implant regions 18. The temperature and duration of this anneal process may vary depending upon the application. In one illustrative embodiment, the anneal process may be performed in an RTA chamber at a temperature ranging from 1000–1200° C. for a duration of approximately 5–10 seconds.

As implanted, the implant regions 18 may have a profile defined by the line 62 and a depth 64, as shown in FIG. 5A. FIG. 5B depicts profiles the implant regions 18 may assume after one or more anneal processes have been performed in, for example, an RTA chamber. In this illustrative embodiment, the post-anneal profile of the implant region 18 after the anneal process is performed is indicated by the line 66, and it has a post-anneal depth 68.

With the decrease in modem device dimensions, and the increase in packing density, it is very important to be able to accurately and reliably determine one or more characteristics of the implant regions 18 after the anneal process is performed on the implant regions 18. According to the present invention, the effectiveness of the anneal process is monitored based upon scatterometric measurements of one or more characteristics of a profile of the implant regions 18 as the anneal process is being performed and/or after it is completed. In the present invention, the values for the dispersion coefficients, i.e., index of refraction (n) and dielectric constant (k), constant or allowing them to vary. It is believed that the most accurate measurement data may be obtained by allowing the values of "n" and "k" to vary as a function of depth. That is, due to the graduation in the concentration of the dopant atoms in the implant regions 18, the values of "n" and "k" also vary. Even more specifically, the concentration of dopant atoms will, in one embodiment, be greater toward the surface 21 of the substrate and the concentration will tend to decrease with increasing depth into the substrate. In other embodiments, the ion implant process may be performed such that the peak concentration of dopant atoms is at a certain depth below the surface 21 of the substrate 10. By varying the values of "n" and/or "k" with depth, a more accurate depiction of the implant profile may be determined.

The present invention may also, however, be employed when the values of "n" and "k" are assumed to be constant through the depth of the implant regions 18. While the data obtained using constant values for "n" and "k" may not, in some cases, be as accurate as the data obtained wherein the values for "n" and "k" are allowed to vary, such data may still be sufficiently accurate for the purposes described herein. Moreover, the data obtained using either technique (constant values for "n" and "k" or varied values for "n" and "k") may be associated with implant profiles determined by other metrology techniques, including destructive metrology techniques. For example, using either technique, a scatterometric profile trace may be taken of one or more of the implant regions 18 after the anneal process is performed on the implant region 18. Thereafter, the implant region 18 may be cross-sectioned and the various parameters of the implant region 18 may then be determined by any of a variety of different metrology techniques, e.g., visual observation of the implant region 18 using a scanning electron microscope, chemical testing for dopant concentrations, etc. Then, the generated profile trace may be associated with the empirical test data. If a subsequently measured implant region 18 results in a generated profile trace that corresponds to or matches the profile trace of the cross-sectional implant region 18, then the later measured implant region 18 may be assumed to exhibit the same characteristics, e.g., depth, concentration profile, as that of the cross-sectional implant region 18.

Figure 6:
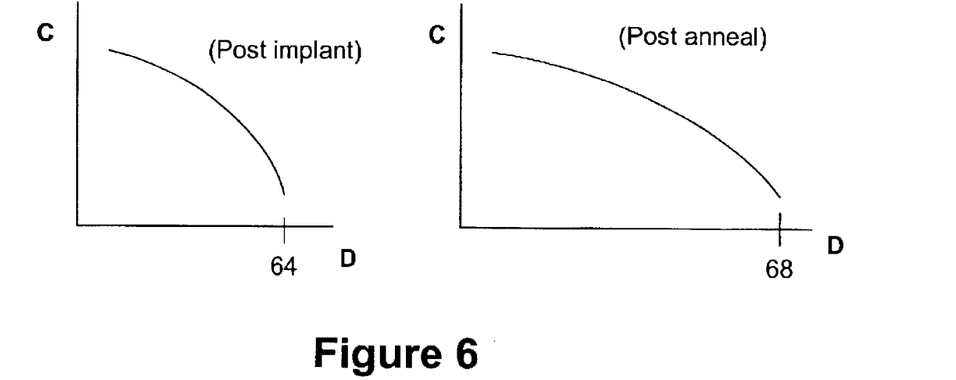
FIG. 6 is a graphical depiction of the concentration profile of the doped regions shown in FIGS. 5A–5B as a function of depth.

FIGS. 5A–5B will now be discussed in the context of where the values of the dispersion coefficients "n" and "k" may be varied. In FIG. 5A, the line 62 is an illustrative depiction of the outline of the implant regions 18 shown therein after the implant process is performed. In FIG. 5B, the line 66 depicts the outline of the implant regions 18 after one or more anneal processes have been performed on the implant regions 18. The original outline 62 of the implant regions 18, as implanted, is depicted by the dashed lines shown in FIG. 5B. As can be seen from FIG. 5B, the dopant materials tend to migrate in an approximately isotropic nature due to the anneal process. FIG. 6 includes graphical depictions of the dopant concentration "C" as a function of depth "D" of the doped regions 18 after implant (left-most graph) and after anneal (right-most graph). As can be seen from these plots, in one embodiment, the dopant concentration is higher toward the surface 21 of the substrate 10 and decreases with increasing depth into the substrate 10.

According to one embodiment of the present invention, the values of "n" and "k" are varied with the depth of the implant regions 18. That is, as shown in FIG. 5A, the implant regions 18 may be, in effect, modeled as several different layers 70a, 70b, 70c and 70d wherein the values of "n" and "k" for each layer may be different. In FIG. 5B, additional layers 70e and 70f may be added to account for the additional depth of the implant regions 18 after the anneal process. The number, thickness and location of the various layers 70a–70f may vary depending upon the particular application. Moreover, the thickness of all of the various layers 70a–70f need not be the same, and the values for "n" and/or "k" may not change at every layer 70a–70f. That is, for example, more than one layer 70a–70f may exhibit the same value for "n." Moreover, the variations in "n" and "k" values between layers 70a–70f need not be linear. In one illustrative embodiment, the thickness of the layers 70a–70f may each be approximately 10–20 nm.

By allowing the "n" and "k" values to vary with depth, a more accurate representation of one or more characteristics of the implant regions 18 may be determined. The values for "n" and "k" may be estimated for every layer 70a–70f, and these estimated values for "n" and "k" may be used as part of the process of establishing a characteristic signature or profile trace, associated with a particular implant profile or characteristic of an implant profile. Such a signature or profile trace may be calculated (using Maxwell's equations and rigorous coupled wave analysis (RCWA)) for a vast variety, if not all, possible combinations of implant profiles readily anticipated by the design process. The correlation between the scatterometry profile trace and the actual implant region 18 profile may be based on a variety of characteristics or factors, including, but not limited to, the width 17 and the depth 19 of the implant regions 18, the concentration of the dopant material, and the dopant concentration profile.

Variations in one or more of the characteristics will cause a significant change in the diffraction characteristics of the incident light from the light source 20. Thus, using scatterometric techniques, a unique profile trace may be established for each unique combination of implant profile characteristics, e.g., depth, width, concentration, etc. A library of profile traces corresponding to each unique combination of implant profile characteristics may be generated and stored in a library. Scatterometry libraries are commercially available from Timbre Technologies, Inc. Although not necessary, if desired, the library of calculated profile traces may be confirmed by various destructive metrology tests, where a scatterometry profile trace is generated and the actual profile of the features is subsequently measured using a cross sectional tunneling electron microscope metrology technique. Obviously, the number of combinations used to create the library may vary as a matter of design choice. Moreover, the greater the number of combinations, the greater will be the library containing the appropriate signature profiles of the implant regions. In some embodiments of the invention, by allowing "n" and "k" to vary with depth, the library of signature traces may be relatively large due to the additional variables in the values for "n" and "k." However, given the importance of accurately forming various implant regions 18 in a substrate 10, the additional computing power and storage required may be warranted.

Figure 7:
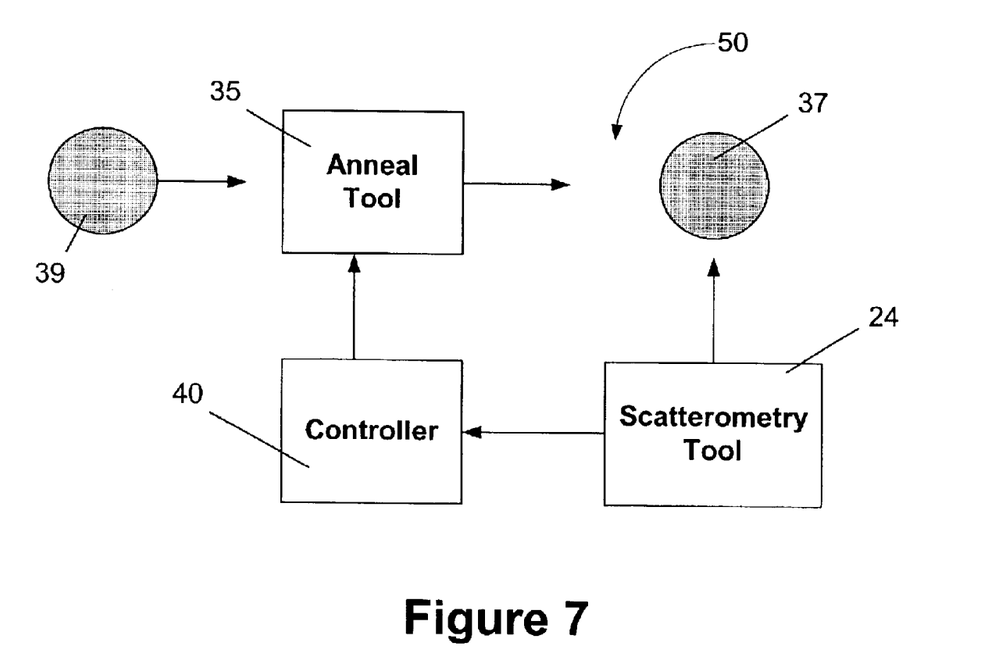
FIG. 7 is a schematic representation of an illustrative system in which the present invention may be employed.

FIG. 7 depicts an illustrative system 50 that may be employed with the present invention. As shown therein, the system 50 is comprised of a scatterometry tool 24, a controller 40, and an anneal tool 35. The scatterometry tool 24 is used to measure one or more of the implanted regions 18 formed on wafers 37 that have been processed through the anneal tool 35 or are being processed in the anneal tool 35. Based upon this measurement, the scatterometry tool 24 is used to generate a profile trace for the measured implant region 18. Thereafter, in one embodiment of the present invention, the generated profile trace of the implant region 18 is compared to a preselected target profile trace. The preselected target profile trace corresponds to a desired characteristic of the implant regions 18 after the anneal process is performed, e.g., implant profiles of a certain desired depth or concentration profile. The target profile trace may be created by varying the values for "n" and "k" as a function of depth and using Maxwell's equations (using these varied values of "n" and "k") to derive the target profile trace or by using constant values for "n" and "k" to derive the target profile trace. A determination is then made, by either the controller 40 or the scatterometry tool 24, if there is a deviation between the generated (or measured) profile trace and the target profile trace. If so, the controller 40 may then change one or more parameters of the operating recipe of the anneal tool 35, such that implanted regions 18 formed in the subsequently processed wafers 39 are closer to the target profile after they are subjected to the anneal process in the anneal tool 35. For example, one or more parameters of the anneal process, e.g., temperature, duration, etc., to be performed on the subsequently processed wafers 39 may be adjusted to achieve the target implant profile for the implant regions 18 after the anneal process is performed.

In another embodiment, the present invention may be employed to compare a generated profile trace to a library of traces, each of which corresponds to a particular anticipated implant profile. That is, in this embodiment, the method comprises generating additional profile traces for implant regions 18 having different post-anneal implant profiles, and establishing a library comprised of a plurality of the post-anneal profile traces, wherein each of the plurality of traces in the library is correlated to a particular implant profile. The traces in the library may all be created on the basis of values for "n" and "k" that are allowed to vary based upon depth into the substrate or based upon constant values for "n" and "k." Thereafter, using known matching techniques, the generated profile trace (from the scatterometry tool) may be matched to the closest corresponding trace in the library. Based upon this match, the measured implant region 18 is determined to have a post-anneal implant profile that corresponds to the post-anneal implant profile associated with the matched trace from the library. Of course, it should be understood that the present invention may be employed in situations where the scatterometric measurements of the implant regions 18 are taken before the anneal process is complete. For example, scatterometric measurements may be taken as the anneal process is being performed. In these cases, the library will contain profile traces that are based upon the anticipated profile of the implant regions 18 at some point during the anneal process, e.g., mid-way, when the process is 90% complete, etc. Thus, use of the term "post-anneal" should encompass situations where the anneal process is actually completed and those situations where only a portion of the anneal process is performed. The same holds true for those applications where a target profile trace is employed.

The effectiveness of the anneal process may then be determined based upon the implant profile of the implant region 18 determined by the scatterometric measurement techniques. The effectiveness of the anneal process may be determined based upon one or more characteristics of the determined implant profile, such as depth, concentration, width, etc. The closer the determined characteristics of the determined implant profile are to target values for the characteristics, the more efficient the anneal process. For example, if, after the anneal process, one or more characteristics of the implant profile of an implant region vary greatly from a target value for the characteristics, the anneal process may be deemed to be less effective. Conversely, the closer the characteristics of the implant profile are to target values for these characteristics, the more effective the anneal process.

The scatterometry tool 24 is used to generate a profile trace for a given structure 11 with implant regions 18 formed thereon. The scatterometry tool 24 may sample one or more structures 11 in a given wafer in a lot or even generate a profile trace for each structure 11 in the lot, depending on the specific implementation. Moreover, the profile traces from a sample of the structures 11 may be averaged or otherwise statistically analyzed. A controller, either in the scatterometry tool 24 or elsewhere in the manufacturing plant, e.g., controller 40, then compares the profile trace (i.e., individual or averaged) generated by the scatterometry tool 24 to a library of calculated profile traces with known implant region profiles to correlate or match the generated or measured profile trace to a trace from the library having an associated implant region profile.

Based on the determined implant region profile, control equations may be employed to adjust the operating recipe of the anneal tool 35 to, for example, account for deviations between the measured post-anneal implant profile and the target post-anneal implant profile. The control equations may be developed empirically using commonly known linear or nonlinear techniques. The controller 40 may automatically control the operating recipes of the anneal tool 35 used to form implant regions 18 on subsequently processed wafers 39. Through use of the present invention, the deviations between the profiles of post-anneal implant regions formed on subsequently processed wafers and a target post-anneal implant profile may be reduced.

In the illustrated embodiment, the controller 40 is a computer programmed with software ware to implement the functions described herein. Moreover, the functions described for the controller 40 may be performed by one or more controllers spread through the system. For example, the controller 40 may be a fab level controller that is used to control processing operations throughout all or a portion of a semiconductor manufacturing facility. Alternatively, the controller 40 may be a lower level computer that controls only portions or cells of the manufacturing facility. Moreover, the controller 40 may be a stand-alone device, or it may reside on the implant tool 35. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 40, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81–0699-Provisional Specification for CIM Framework Domain Architecture) and APC (SEMI E93–0999-Provisional Specification for CIM Framework Advanced Process Control Component) specifications are publicly available from SEMI.

The present invention is directed to several inventive methods. In one embodiment, the method comprises forming a first plurality of implant regions in a semiconducting substrate, performing at least one anneal process on the implant regions, performing a scatterometric measurement of at least one of the implant regions after at least a portion of the anneal process is performed to determine a profile of the implant region and determining an effectiveness of the anneal process based upon the determined profile of the implant region.

Through use of the present invention, anneal processes performed on implant regions 18 may be more effectively monitored. As a result, better control of the location, size and concentration profile of such implant regions 18 may be achieved. In turn, this may result in improved device performance and enhanced product yields.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of monitoring an anneal process performed on an implant region, comprising:

forming a first plurality of implant regions in a semiconducting substrate;

performing at least one anneal process on said first plurality of implant regions;

performing a scatterometric measurement of at least one of said first plurality of implant regions after at least a portion of said anneal process is performed to determine an implant profile of said at least one implant region; and determining an effectiveness of said at least one anneal process based upon said determined profile of said at least one implant region.

2. The method of claim 1, wherein said at least one anneal process is performed in at least one of a furnace and a rapid thermal anneal chamber.

3. The method of claim 1, wherein said at least one anneal process is performed to activate dopant atoms implanted into said first plurality of implant regions.

4. The method of claim 1, wherein said at least one anneal process is performed at a temperature that ranges from approximately 1000–1200□C.

5. The method of claim 1, wherein performing said scatterometric measurement of said at least one implant region comprises illuminating at least one of said first plurality of implant regions and measuring light reflected therefrom.

6. The method of claim 1, wherein performing said scatterometric measurement of said at least one implant region comprises:

generating a profile trace for said at least one implant region;

creating a profile trace for an anticipated profile of said at least one implant region; and comparing said generated profile trace to said created profile trace.

7. The method of claim 6, wherein said created profile trace is created based upon assumed constant values for an index of refraction and a dielectric constant.

8. The method of claim 6, wherein values of at least one of an index of refraction and a dielectric constant are varied in creating said created profile trace.

9. The method of claim 6, further comprising modifying, based upon said comparison of said generated profile trace and said created profile trace, at least one parameter of an anneal process to be performed on implant regions formed on a subsequently processed substrate.

10. The method of claim 9, wherein modifying at least one parameter of said anneal process comprises modifying at least one of a temperature and a duration of said at least one anneal process.

11. The method of claim 1, further comprising creating a library comprised of a plurality of created profile traces, wherein said created profile traces are representative of implant regions having varying implant profiles.

12. The method of claim 1, wherein performing said scatterometric measurement of said at least one implant region comprises:

generating a profile trace for said at least one implant region;

creating a target profile trace for said at least one implant region; and comparing said generated profile trace to said target profile trace.

13. The method of claim 12, wherein said target profile trace is created based upon assumed constant values for an index of refraction and a dielectric constant.

14. The method of claim 12, wherein values of at least one of an index of refraction and a dielectric constant are varied in creating said target profile trace.

15. The method of claim 12, further comprising modifying, based upon said comparison of said generated profile trace and said target profile trace, at least one parameter of an anneal process to be performed on implant regions formed on a subsequently processed substrate.

16. The method of claim 1, wherein forming a first plurality of implant regions in said substrate comprises forming a first plurality of implant regions to thereby define a grating structure in said substrate.

17. The method of claim 1, wherein said first plurality of implant regions are comprised of N type dopant material or P type dopant material.

18. The method of claim 1, wherein said first plurality of implant regions are illuminated using at least one of a multiple wavelength light source and a single wavelength light source.

19. The method of claim 1, wherein said determined implant profile is comprised of at least one of a width, a depth, a dopant concentration level, and a dopant concentration profile of said implant regions.

20. The method of claim 1, further comprising modifying, based upon said determined effectiveness of said at least one anneal process, at least one parameter of an anneal process to be performed on implant regions formed and on a subsequently processed substrate.

21. The method of claim 20, wherein modifying at least one parameter of said anneal process comprises modifying at least one of a temperature and a duration of said at least one anneal process.

22. The method of claim 1, wherein said scatterometric measurement employs constant values for an index of refraction and a dielectric constant.

23. The method of claim 1, wherein said scatterometric measurement employs varied values for at least one of an index of refraction and a dielectric constant.

24. The method of claim 23, wherein said values of at least one of said index of refraction and said dielectric constant are varied based upon depth.

25. The method of claim 1, wherein said scatterometric measurement is performed after said at least one anneal process is completed.

26. A method of monitoring an anneal process performed on an implant region, comprising:

forming a first plurality of implant regions in a semiconducting substrate;

performing at least one anneal process on said first plurality of implant regions;

performing a scatterometric measurement of at least one of said first plurality of implant regions after said anneal process is complete to determine an implant profile of said at least one implant region;

determining an effectiveness of said at least one anneal process based upon said determined profile of said at least one implant region; and modifying, based upon said determined effectiveness of said at least one anneal process, at least one parameter of an anneal process to be performed on implant regions formed on a subsequently processed substrate.

27. The method of claim 26, wherein said at least one anneal process is performed in at least one of a furnace and a rapid thermal anneal chamber.

28. The method of claim 26, wherein said at least one anneal process is performed to activate dopant atoms implanted into said first plurality of implant regions.

29. The method of claim 26, wherein said at least one anneal process is performed at a temperature that ranges from approximately 1000–1200□C.

30. The method of claim 26, wherein performing said scatterometric measurement of said at least one implant region comprises illuminating at least one of said fast plurality of implant regions and measuring light reflected therefrom.

31. The method of claim 26, wherein performing said scatterometric measurement of said at least one implant region comprises:

generating a profile trace for said at least one implant region;

creating a profile trace for an anticipated profile of said at least one implant region; and comparing said generated profile trace to said created profile trace.

32. The method of claim 31, wherein said created profile trace is created based upon assumed constant values for an index of refraction and a dielectric constant.

33. The method of claim 31, wherein values of at least one of an index of refraction and a dielectric constant are varied in creating said created profile trace.

34. The method of claim 31, further comprising modifying, based upon said comparison of said generated profile trace and said created profile trace, at least one parameter of an anneal process to be performed on implant regions formed on a subsequently processed substrate.

35. The method of claim 34, wherein modifying at least one parameter of said anneal process comprises modifying at least one of a temperature and a duration of said at least one anneal process.

36. The method of claim 26, further comprising creating a library comprised of a plurality of created profile traces, wherein said created profile traces are representative of implant regions having varying implant profiles.

37. The method of claim 26, wherein performing said scatterometric measurement of said at least one implant region comprises:
generating a profile trace for said at least one implant region;
creating a target profile trace for said at least one implant region; and
comparing said generated profile trace to said target profile trace.

38. The method of claim 37, wherein said target profile trace is created based upon assumed constant values for an index of refraction and a dielectric constant.

39. The method of claim 37, wherein values of at least one of an index of refraction and a dielectric constant are varied in creating said target profile trace.

40. The method of claim 37, further comprising modifying, based upon said comparison of said generated profile trace and said target profile trace, at least one parameter of an anneal process to be performed on implant regions formed on a subsequently processed substrate.

41. The method of claim 26, wherein forming a first plurality of implant regions in said substrate comprises forming a first plurality of implant regions to thereby define a grating structure in said substrate.

42. The method of claim 26, wherein said first plurality of implant regions are comprised of N type dopant material or P type dopant material.

43. The method of claim 26, wherein said first plurality of implant regions are illuminated using at least one of a multiple wavelength light source and a single wavelength light source.

44. The method of claim 26, wherein said determined implant profile is comprised of at least one of a width, a depth, a dopant concentration level, and a dopant concentration profile of said implant regions.

45. The method of claim 26, wherein modifying at least one parameter of said anneal process comprises modifying at least one of a temperature and a duration of said at least one anneal process.

46. The method of claim 26, wherein said scatterometric measurement employs constant values for an index of refraction and a dielectric constant.

47. The method of claim 26, wherein said scatterometric measurement employs varied values for at least one of an index of refraction and a dielectric constant.

48. The method of claim 47, wherein said values of at least one of said index of refraction and said dielectric constant are varied based upon depth.

49. A method of monitoring an anneal process performed on an implant region, comprising:
forming a first plurality of implant regions in a semiconducting substrate;
performing at least one anneal process on said first plurality of implant regions;
performing a scatterometric measurement of at least one of said first plurality of implant regions after said anneal process is completed to determine an implant profile of said at least one implant region by:
generating a profile truce for said at least one implant region,
creating a plurality of profile traces, each of which correspond to an anticipated profile of said at least one implant region, and
comparing said generated profile trace to at least one of said created plurality of profile traces, and
determining an effectiveness of said at least one anneal process based upon said determined profile of said at least one implant region.

50. The method of claim 49, wherein said at least one anneal process is performed in at least one of a furnace and a rapid thermal anneal chamber.

51. The method of claim 49, wherein said at least one anneal process is performed to activate dopant atoms implanted into said first plurality of implant regions.

52. The method of claim 49, wherein said at least one anneal process is performed at a temperature that ranges from approximately 1000–1200□C.

53. The method of claim 49, wherein performing said scatterometric measurement of said at least one implant region comprises illuminating at least one of said first plurality of implant regions and measuring light reflected therefrom.

54. The method of claim 49, wherein said plurality of profile trace is created based upon assumed constant values for an index of refraction and a dielectric constant.

55. The method of claim 49, wherein values of at least one of an index of refraction and a dielectric constant are varied in creating said plurality of profile traces.

56. The method of claim 49, further comprising creating a library comprised of said plurality of profile traces.

57. The method of claim 49, wherein forming a first plurality of implant regions in said substrate comprises forming a first plurality of implant regions to thereby define a grating structure in said substrate.

58. The method of claim 49, wherein said first plurality of implant regions are comprised of N type dopant material or P type dopant material.

59. The method of claim 49, wherein said first plurality of implant regions are illuminated using at least one of a multiple wavelength light source and a single wavelength light source.

60. The method of claim 49, wherein said determined implant profile is comprised of at least one of a width, a depth, a dopant concentration level, and a dopant concentration profile of said implant regions.

61. The method of claim 49, further comprising modifying, based upon said determined effectiveness of said at least one anneal process, at least one parameter of an anneal process to be performed on implant regions formed on a subsequently processed substrate.

62. The method of claim 61, wherein modifying at least one parameter of said anneal process comprises modifying at least one of a temperature and a duration of said at least one anneal process.

63. The method of claim 49, further comprising modifying, based upon said comparison of said generated profile trace and at least one of said created profile traces, at least one parameter of an anneal process to be performed on implant regions formed on a subsequently processed substrate.

64. The method of claim 63, wherein modifying at least one parameter of said anneal process comprises modifying at least one of a temperature and a duration of said at least one anneal process.

65. The method of claim 49, wherein said scatterometric measurement employs constant values for an index of refraction and a dielectric constant.

66. The method of claim 49, wherein said scatterometric measurement employs varied values for at least one of an index of refraction and a dielectric constant.

67. The method of claim 66, wherein said values of at least one of said index of refraction and said dielectric constant are varied based upon depth.

68. A method of monitoring an anneal process performed on an implant region, comprising:

forming a first plurality of implant regions in a semiconducting substrate;

performing at least one anneal process on said first plurality of implant regions;

performing a scatterometric measurement of at least one of said first plurality of implant regions after said anneal process is completed to determine an implant profile of said at least one implant region by:

generating a profile trace for said at least one implant region, creating a target profile trace for said at least one implant region, and comparing said generated profile trace to said target profile trace; and determining an effectiveness of said at least one anneal process based upon said determined profile of said at least one implant region.

69. The method of claim 68, wherein said at least one anneal process is performed in at least one of a furnace and a rapid thermal anneal chamber.

70. The method of claim 68, wherein said at least one anneal process is performed to activate dopant atoms implanted into said first plurality of implant regions.

71. The method of claim 68, wherein said at least one anneal process is performed at a temperature that ranges from approximately 1000–1200□C.

72. The method of claim 68, wherein performing said scatterometric measurement of said at least one implant region comprises illuminating at least one of said first plurality of implant regions and measuring light reflected therefrom.

73. The method of claim 68, wherein said target profile trace is created based upon assumed constant values for an index of refraction and a dielectric constant.

74. The method of claim 68, wherein values of at least one of an index of refraction and a dielectric constant are varied in creating said target profile trace.

75. The method of claim 68, further comprising modifying, based upon said comparison of said generated profile trace and said target profile trace, at least one parameter of an anneal process to be performed on implant regions formed on a subsequently processed substrate.

76. The method of claim 68, wherein forming a first plurality of implant regions in said substrate comprises forming a first plurality of implant regions to thereby define a grating structure in said substrate.

77. The method of claim 68, wherein said first plurality of implant regions are comprised of N type dopant material or P type dopant material.

78. The method of claim 68, wherein said first plurality of implant regions are illuminated using at least one of a multiple wavelength light source and a single wavelength light source.

79. The method of claim 68, wherein said determined implant profile is comprised of at least one of a width a depth, a dopant concentration level, and a dopant concentration profile of said implant regions.

80. The method of claim 68, further comprising modifying, based upon said determined effectiveness of said at least one anneal process, at least one parameter of an anneal process to be performed on implant regions formed on a subsequently processed substrate.

81. The method of claim 80, wherein modifying at least one parameter of said anneal process comprises modifying at least one of a temperature and a duration of said at least one anneal process.

82. The method of claim 68, wherein said scatterometric measurement employs constant values for an index of refraction and a dielectric constant.

83. The method of claim 68, wherein said scatterometric measurement employs varied values for at least one of an index of refraction and a dielectric constant.

84. The method of claim 83, wherein said values of at least one of said index of refraction and said dielectric constant are varied based upon depth.

* * * * *

UNITED STATES PATENT AND TRADEMARK OFFICE
CERTIFICATE OF CORRECTION

PATENT NO. : 6,933,158 B1
DATED : August 23, 2005
INVENTOR(S) : Kevin R. Lensing et al.

It is certified that error appears in the above-identified patent and that said Letters Patent is hereby corrected as shown below:

Column 12,
Line 59, change "1000-1200☐C" to -- 1000-1200°C --.

Column 13,
Line 64, after "formed," delete "and".

Column 14,
Line 39, change "1000-1200☐C" to -- 1000-1200°C --.
Line 42, change "fast" to -- first --.

Column 15,
Line 66, change "truce" to -- trace --.

Column 16,
Lines 1-2, change "correspond" to -- corresponds --.
Line 17, change "1000-1200☐C" to -- 1000-1200°C --.
Line 24, change "trace" to -- traces --.

Column 17,
Line 33, change "1000-1200☐C" to -- 1000-1200°C --.

Signed and Sealed this

Twenty-fifth Day of October, 2005

JON W. DUDAS
*Director of the United States Patent and Trademark Office*